US010413663B2

(12) United States Patent
Lee et al.

(10) Patent No.: US 10,413,663 B2
(45) Date of Patent: Sep. 17, 2019

(54) AUTOMATIC ANTI-FREE-FLOW VALVE FOR MEDICAL PUMPS (71) Applicant: Zyno Medical, LLC, Natick, MA (US)

(72) Inventors: Chao Young Lee, Weston, MA (US); Mei Zhang, Sharon, MA (US)

(73) Assignee: Zyno Medical, LLC, Natick, MA (US)

(*) Notice: Subject to any disclaimer, the term of this patent is extended or adjusted under 35 U.S.C. 154(b) by 169 days.

(21) Appl. No.: 15/061,523

(22) Filed: Mar. 4, 2016

(65) Prior Publication Data
US 2017/0252511 A1    Sep. 7, 2017

(51) Int. Cl.
A61M 5/168 (2006.01)
A61M 5/14 (2006.01)
A61M 5/142 (2006.01)
A61M 39/08 (2006.01)
A61M 39/28 (2006.01)
A61M 39/24 (2006.01)

(52) U.S. Cl.
CPC ........ A61M 5/16881 (2013.01); A61M 5/142 (2013.01); A61M 5/1413 (2013.01); A61M 5/14232 (2013.01); A61M 5/16813 (2013.01); A61M 39/08 (2013.01); A61M 39/281 (2013.01); A61M 39/284 (2013.01); A61M 2039/2433 (2013.01)

(58) Field of Classification Search
CPC ............ A61M 5/16881; A61M 5/1413; A61M 5/142; A61M 5/14232; A61M 5/16813; A61M 2039/2426; A61M 2039/2473; A61M 2039/2486; A61M 2039/2433; A61M 39/045; A61M 39/26; A61M 2039/027; A61M 2039/1072; A61M 39/225; A61M 2039/226
See application file for complete search history.

(56) References Cited

U.S. PATENT DOCUMENTS

| 3,965,925 | A  |    | 6/1976 | Gooch |   |
|-----------|----|----|--------|-------|---|
| 5,396,925 | A  |    | 3/1995 | Poli  |   |
| 8,469,933 | B2 |    | 6/2013 | Zhang et al. | |
| 8,752,436 | B2 | *  | 6/2014 | Beck .................. | A61M 5/16854 |
|           |    |    |        |       | 604/506 |
| 2002/0038105 | A1 | * | 3/2002 | Schwartz .............. | A61M 39/24 |
|           |    |    |        |       | 604/247 |
| 2006/0027270 | A1 | * | 2/2006 | Truitt .................... | A61M 39/02 |
|           |    |    |        |       | 137/843 |
| 2006/0030821 | A1 | * | 2/2006 | Lee .................... | A61M 5/16831 |
|           |    |    |        |       | 604/246 |
| 2006/0192164 | A1 | * | 8/2006 | Korogi ............... | A61B 5/15003 |
|           |    |    |        |       | 251/149 |
| 2007/0106228 | A1 | * | 5/2007 | Bell .................... | A61M 1/3627 |
|           |    |    |        |       | 604/247 |
| 2007/0265559 | A1 |    | 11/2007 | Kunishige et al. | |

(Continued)

Primary Examiner — Laura A Bouchelle
Assistant Examiner — Dung T Ulsh
(74) Attorney, Agent, or Firm — Boyle Fredrickson S.C.

(57) ABSTRACT

A valve for a tubing kit used provides a resilient element naturally moving to a closed state to reduce opportunity for inadvertent leakage of medicine and to reduce effort required by healthcare personnel to seal the fluid line. In one embodiment the resilient element is a spring serving to compress the walls of IV tube in the closure and in a second embodiment the resilient element is an elastomeric member that is deformed to provide an opening to allow passage of fluid through the fluid line.

11 Claims, 6 Drawing Sheets (56) References Cited

U.S. PATENT DOCUMENTS

| | | | |
|---|---|---|---|
| 2008/0172006 A1* | 7/2008 | Hicks | A61M 39/223 604/249 |
| 2008/0275590 A1* | 11/2008 | Ross | A61M 5/1483 700/228 |
| 2009/0254034 A1* | 10/2009 | Beck | A61M 39/28 604/118 |
| 2011/0240158 A1* | 10/2011 | Py | A61M 39/18 137/614 |
| 2011/0276035 A1* | 11/2011 | Fangrow, Jr. | A61M 39/26 604/535 |
| 2013/0105603 A1* | 5/2013 | Krankowsky | B08B 5/02 239/532 |
| 2013/0338624 A1* | 12/2013 | Mansour | A61M 5/16813 604/500 |
| 2014/0191501 A1* | 7/2014 | Brugger | F16L 35/00 285/120.1 |
| 2014/0213975 A1* | 7/2014 | Clemente | A61M 5/158 604/151 |
| 2015/0004034 A1* | 1/2015 | Hansen | F04B 43/08 417/474 |
| 2015/0018780 A1* | 1/2015 | Butterfield | A61M 39/22 604/246 |
| 2015/0076815 A1* | 3/2015 | Lombardi, III | A61M 39/1011 285/317 |
| 2015/0258277 A1* | 9/2015 | Halpert | A61M 5/1723 604/503 |
| 2015/0335852 A1* | 11/2015 | Miller | A61M 16/0808 251/304 |
| 2018/0015278 A1* | 1/2018 | Ueda | A61M 39/10 |

* cited by examiner

AUTOMATIC ANTI-FREE-FLOW VALVE FOR MEDICAL PUMPS

CROSS REFERENCE TO RELATED APPLICATION

--

BACKGROUND OF THE INVENTION

The present invention relates to medical pumps for the delivery of medicines to patients and in particular to an anti-free-flow valve integrated to a tubing kit and limiting accidental release of medicine prior to the tubing kit being installed in the medical pump or as it is being removed from the pump.

Medical pumps, such as syringe pumps or peristaltic infusion pumps, are known for computer-controlled delivery of medication or contrast agents (henceforth drugs) to patients over a period of time. Typically, the drug is provided in a syringe or a flexible bag that may be connected to a fluid line attached to a needle for insertion into the patient.

When a nurse or other health care professional ministering to the patient receives the drug, for example, in a flexible bag, the fluid line must be attached, typically by inserting a fluid line spike attached to one end of the flexible tubing into the bag. During a priming process, fluid from the bag is allowed to flow through the fluid line to purge bubbles from the fluid line and then the fluid line is installed in the pump typically by threading the fluid line through compressive fingers of a peristaltic pump. During the first steps of priming the fluid line, it is important that any clamps on the fluid line be open. After a purging of air from the line, the clamps are closed to prevent leakage until the fluid line is loaded into the pump. Immediately before loading of the fluid line into the pump, however, the clamps that were closed must be opened again so that the pump may operate without obstruction. When the fluid line is taken out of the pump at any point, it is important to ensure the line is closed and there is no uncontrolled fluid freely flowing to patient body. However, the caregiver may forget to close clamp manually. In some situations, such mistake has serious consequences. A valve that automatically closes when the fluid line is released from the pump can avoid such undesired situations and could save lives in critical scenarios.

U.S. Pat. No. 8,469,933 entitled "Pump Activated Pinch Valve", assigned to the assignee of the present invention and hereby incorporated by reference, discloses a valve for a fluid line that may be closed about the fluid line after priming of the fluid line and bag to prevent fluid leakage and then installed in the pump in a closed state. When the door of the medical pump is closed, the clamp automatically opens. In this way preparation of the fluid line and installing it to the pump is greatly simplified with reduced risk of leakage while also preventing unintended blockage of the flow of medicine. The clamp provides a single piece plastic element having a natural resilience tending to move it to an open position. The clamp element is compressed against this resilience to close the fluid line and held in that close position by a catch. The catch is automatically released by an element on the pump door once the clamp element is installed on the pump and the door is closed.

SUMMARY OF THE INVENTION

The present invention provides valve that may be automatically released by a medical pump after it is installed in the pump. In contrast to the valve described above, however, a resilient element in the valve closes the fluid line in a relaxed rather than a compressed state. Because the valve is normally closed in the relaxed state, inadvertent leakage is less likely and the force required to close the fluid line reduced. The valve design provides a more compact form factor compatible with a wide variety of medical pumps.

In one embodiment, the invention provides a fluid line kit having a length of flexible tubing terminating at opposed first and second ends and a valve mechanically retained on the IV tubing between the first and second ends. The valve includes a housing positioned between a first and second portion of the IV tubing and a fluid blocking element positioned within the housing and resiliently biased to block fluid flow in a relaxed state and to permit fluid flow in a compressed state. The valve is configured to permit a feature from a medical pump to compress the fluid blocking element from the relaxed state to the compressed state when the fluid line kit is installed in the medical pump.

It is thus a feature of at least one embodiment of the invention to provide a simple valve for a fluid line kit that is normally in a closed position. It is another feature of at least one embodiment of the invention to provide a valve whose natural resilience aids in closure, reducing the forces required to close the valve by the user.

The housing may provide a first tube extending along an axis in an axial telescopic sliding relationship with a second tube, the first and second tubes having passageways extending transversely through opposed walls of the tubes perpendicular to the axis and further including a spring biasing the first and second tube apart along the axis. The opening in the second tube may provide the fluid blocking element operating, when the fluid line is threaded through the passageways of the first and second tubes, to compress the fluid line to prevent flow therethrough in the relaxed state when the passageways through the first and second tubes are displaced from alignment and to release the fluid line in the relaxed state when the passageways through the first and second tubes are aligned.

It is thus a feature of at least one embodiment of the invention to provide a simple valve that may work external to the IV tubing to avoid the need for contact between the valve elements and the fluid in the IV tubing.

The first and second tubes may provide interengaging lock elements holding the valve in the compressed state when the lock elements are engaged and releasing the valve to the relaxed state when the lock elements are released.

It is thus a feature of at least one embodiment of the invention to allow the fluid line to be easily commissioned and to reduce cold flow of the fluid line during storage of the tubing kit by providing an interlock holding the valve in the compressed state.

The interengaging lock elements may be disengaged by relative rotation of the first and second tubes along the axis.

It is thus a feature of at least one embodiment of the invention to allow simple release of the valve by rotation of the elements without the need for a tool or the like.

The lock element may include a radially extending pin on one of the first and second tubes and an axial slot on another of the first and second tubes providing a catch location releasable by relative rotation of the first and second tubes.

It is thus a feature of at least one embodiment of the invention to provide a simple interlock system that may be readily fabricated when these parts are constructed according to injection molding techniques.

A passageway in at least one of the first and second tubes may be substantially larger than the fluid line to allow axial rotation of the first and second tubes with respect to each other.

It is thus a feature of at least one embodiment of the invention to prevent the fluid line from blocking rotational adjustment of the valve.

The spring element may be a helical compression spring contained within at least one of the first and second tubes.

It is thus a feature of at least one embodiment of the invention to permit the use of a metallic spring element resistant to cold flow and memory under long periods of compression.

In a second embodiment, the housing may provide a tubular sleeve having an internal chamber communicating with the IV tubing extending axially from connections on opposite sides of the tubular sleeve so that the internal chamber is positioned along the flow path between the IV tubing on opposite sides of the tubular sleeve.

It is thus a feature of at least one embodiment of the invention to provide an in-line valve that need not deform the fluid line of the tubing meeting any constraints requiring high forces or specially compliant IV line material or problems related to permit deformation of the fluid line.

The tubular sleeve may hold a resilient elastomer element in a relaxed state filling at least a portion of the tubular sleeve to block fluid flow between the connections and in a compressed state allowing fluid flow between the connections.

It is thus a feature of at least one embodiment of the invention to produce a valve using a resilient element that can be tailored to the desired forces and properties needed.

The elastomeric element may include a slot through the elastomer element that is closed when the elastomer element is in a relaxed state and open when the elastomer element is in a compressed state.

It is thus a feature of at least one embodiment of the invention to provide an extremely simple valve element in which the valve and resilient elements are integrated.

The valve may alternatively include a plunger for compressing the elastomer element away from the connectors in a compressed state so that fluid flow may pass around the plunger and the elastomer element is displaced away from the fluid flow.

It is thus a feature of at least one embodiment of the invention to provide a simple valve element providing a sweeping action of the valve element tending to clear debris from the valve channel for more robust closure.

The plunger may include a seal displaced from the plunger to prevent outflow from the tubular sleeve when fluid flow passes around the plunger.

It is thus a feature of at least one embodiment of the invention to ensure leak-proof operation when the valve is in the open state.

The valve may include a compressor removably attaching to the housing to hold the elastomer element in the compressed state when the compressor is attached to the housing.

It is thus a feature of at least one embodiment of the invention to permit ready priming of the fluid line in which the valve is ideally held in an open state.

These particular objects and advantages may apply to only some embodiments falling within the claims and thus do not define the scope of the invention.

DETAILED DESCRIPTION OF THE PREFERRED EMBODIMENT

Figure 1:
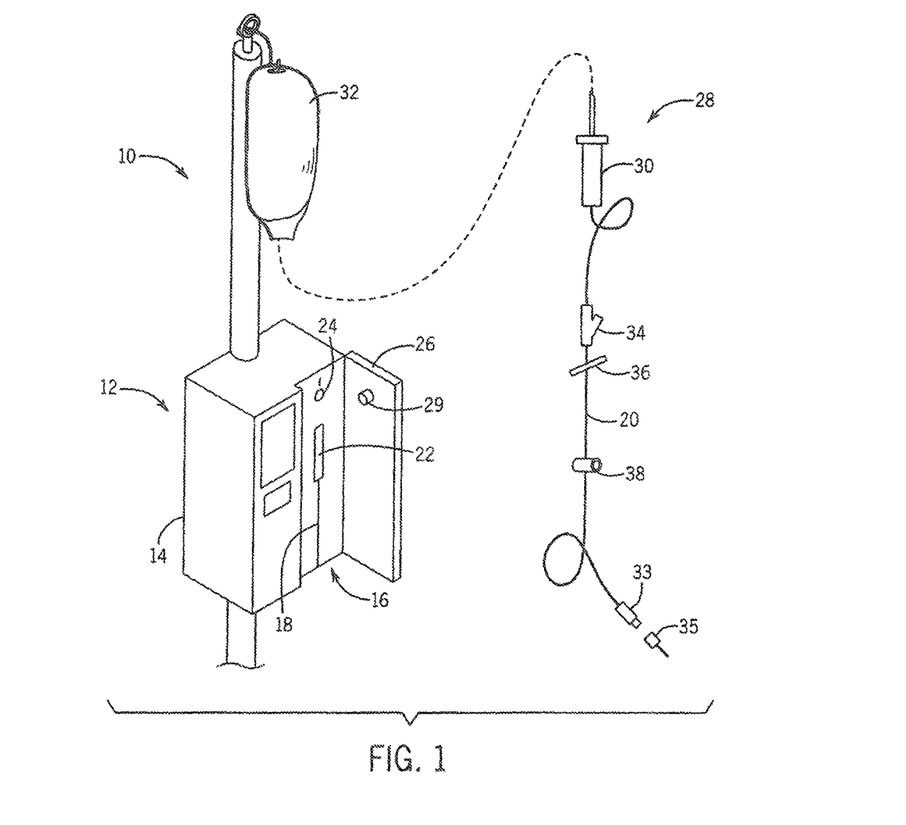
FIG. 1 is a simplified perspective view of an infusion pump and medicine bag, the latter of which may be attached to a tubing kit by means of a bag spike on one end of a fluid line leading to a luer lock, the fluid line having an intervening valve that may be automatically operated by the infusion pump.

Referring now to FIG. 1, a medical pump assembly 10, for example, may include an infusion pump 12 having a housing 14 incorporating a pump compartment 16 providing a channel 18 through which a fluid line 20 may be threaded. The pump compartment 16 may expose pump elements 22 that may compress the fluid line 20 to provide peristaltic pumping action as is generally understood in the art. In addition, the pump compartment 16 may provide for a valve retention socket 24 as will be discussed in detail below. The pump compartment 16 may be covered by a hinged pump door 26 having a valve operating compressor 29 aligned with the socket 24 to activate a valve in the socket 24 when the door 26 is closed and latched.

The fluid line 20 may be part of a fluid line kit 28 providing the fluid line 20 an IV bag spike 30 that may be used to connect to an IV bag 32 as is generally understood in the art. An opposite end of the fluid line 20 may have a Luer lock 33, for example, to connect with a hypodermic needle 35 or the like. Other features may be found on the fluid line including an injection port 34 for joining the fluid line 20 with other lines or providing for the admission of other fluids into the fluid line, and a standard IV line roller clamp or slide clamp 36. Per the present invention, the fluid line 20 will provide valve 38 of the present invention either fixed to the fluid line 20 along its length or slidable on the fluid line 20 but constrained by the spike 30 and luer lock 33 against removal from the fluid line 20.

Figure 2:
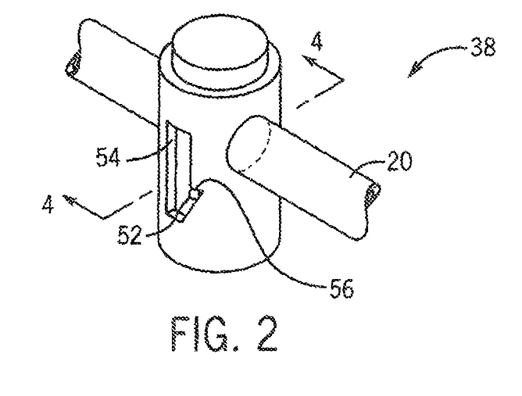
FIG. 2 is a fragmentary perspective view of the valve of FIG. 1 as positioned on the fluid line in a first embodiment.
Figure 3:
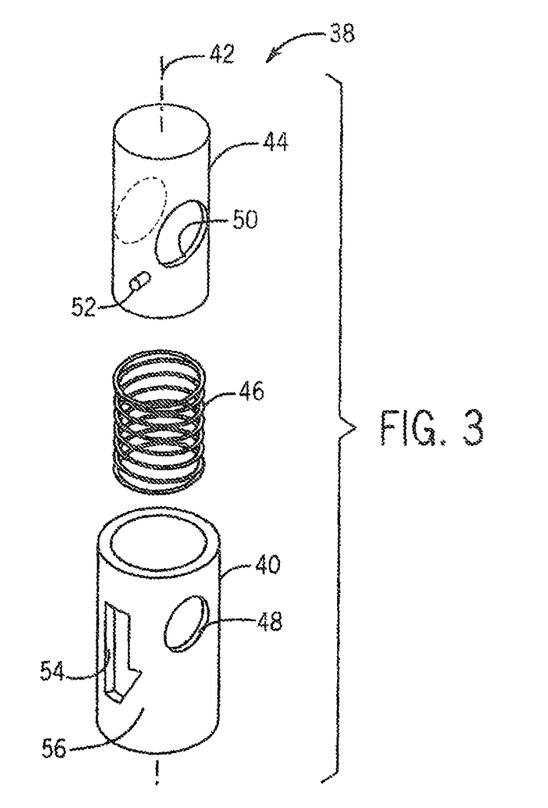
FIG. 3 is an exploded perspective view of the valve of FIG. 2.

Referring now to FIGS. 2 and 3, in a first embodiment, the valve 38 may have an outer tube 40 defining a generally cylindrical cavity closed at the bottom end extending along an axis 42. A second inner tube 44 has an outer diameter to be received within the cavity of the outer tube 40 in telescopic fashion to slide therein. A helical compression spring 46 fits between the bottom of outer tube 40 and the bottom of inner tube 44 to bias them apart along axis 42.

Each of the outer tube 40 and inner tube 44 has transverse holes 48 and 50, respectively, extending perpendicularly to axis 42 through opposite sidewalls of each outer tube 40 and inner tube 44. When the holes 48 and 50 are aligned by movement of these inner tubes 44 and compression of spring 46, the fluid line 20 may be threaded through the assembly as shown in FIG. 2 to pass both through aligned openings 48 and 50. Generally hole 48 will be sized to be close to the diameter of the fluid line 20 whereas hole 50 will be larger to permit axial rotation of the inner tube 44 when hole 50 receives the fluid line 20.

Figure 4A:
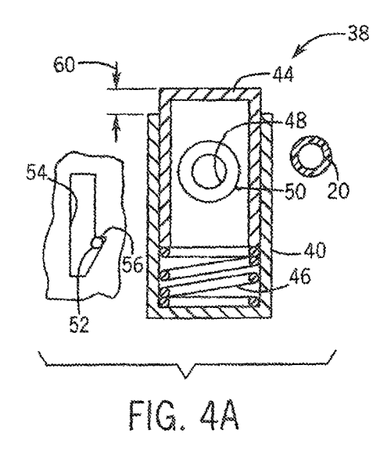
FIGS. 4a-4c are cross-sectional views along line 4-4 of FIG. 2 showing respectively: the valve in a first compressed state allowing free flow of liquid through the fluid line during IV line priming, the valve in a relaxed state blocking fluid flow through the fluid line, and the valve in a second compressed state allowing fluid flow through the fluid line when activated by the pump.
Figure 4B:
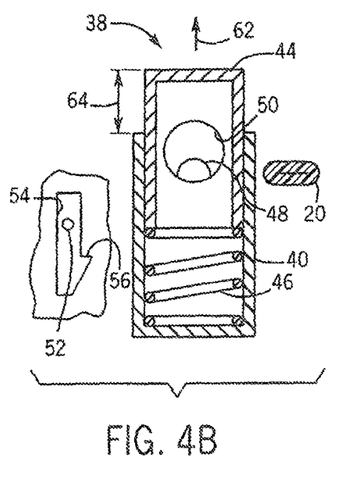

A sidewall of inner tube 44 may have a radially extending pin 52 received within a corresponding axially extending slot 54 in an outer wall of outer tube 40. As inner tube 44 moves axially within outer tube 40, pin 52 may move axially along slot 54. Slot 54 may have a catch ledge 56 extending circumferentially outward from one of its axial walls. This catch ledge 56 may capture the pin 52 against upward axial movement under the biasing force of the spring 46 as shown generally in FIG. 4a. When the pin 52 is so captured, the inner tube 44 will be held fully retracted in outer tube 40, compressing helical compression spring 46 so that inner tube 44 extends out from outer tube 40 by a priming distance 60. At this priming distance 60, holes 50 and 48 are non-overlapping but not perfectly centered, with hole 48 being displaced toward the top edge of hole 50 as depicted. Nevertheless, the fluid line 20 (depicted to the side for clarity) inserted through the holes 50 and 48 will be uncompressed allowing free flow of liquid. This mode may be used during priming of the fluid line.

Figure 4C:
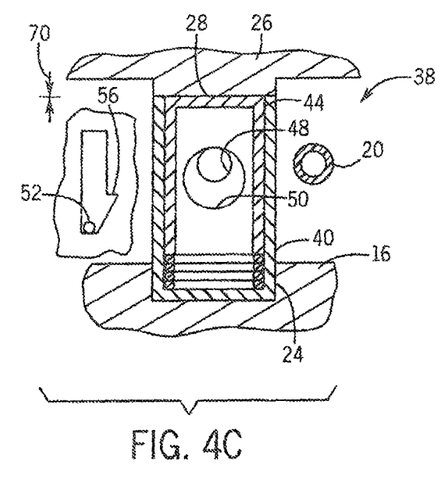

Referring now to FIG. 4c, a slight downward compression of inner tube 44 with respect to outer tube 40 will cause pin 52 to rotate leftward guided by an inwardly sloping wall beneath the catch ledge 56 pushing the pin 52 beyond the ledge 56 so that it may move upward in the slot 54 (as shown in FIG. 4c) allowing relaxation of the compression spring 46 and inner tube 44 to move upward as indicated by arrow 62 to an extension distance 64. At this extension distance 64, hole 50 will partially occlude hole 48 causing IV line 20 to be compressed into a closed state not allowing liquid to flow through the fluid line 20. The force of the spring 46 is sufficient to provide for this compression of the fluid line 20. It should be noted that the spring 46 operates to perform the compression thus relieving the user of the need to provide a force on inner tube 44 sufficient for this compression process as is necessary in the prior art.

Referring now to FIGS. 1 and 4c, the outer tube 40 may fit within a socket 24 in the pump compartment 16 when the fluid line 20 is installed in the pump 12 so that when the valve 38 is inserted into the pump 12 and the door 26 is closed, a compressor 29 on the door 26 compresses inner tube 44 downward to extend by an operating distance 70 from outer tube 40. At the operating distance 70, holes 48 and 50 are aligned (concentric) releasing IV line 20 to allow free fluid flow. Note that this operating distance 70 is generally less than distance 60 so that there is no danger of pin 52 being captured by ledge 56 when the inner tube 44 is at the compression distance.

Generally the inner tube 44 and outer tube 40 may be constructed from injection molded thermoplastic and the helical spring 46 from a stainless steel.

Figure 5:
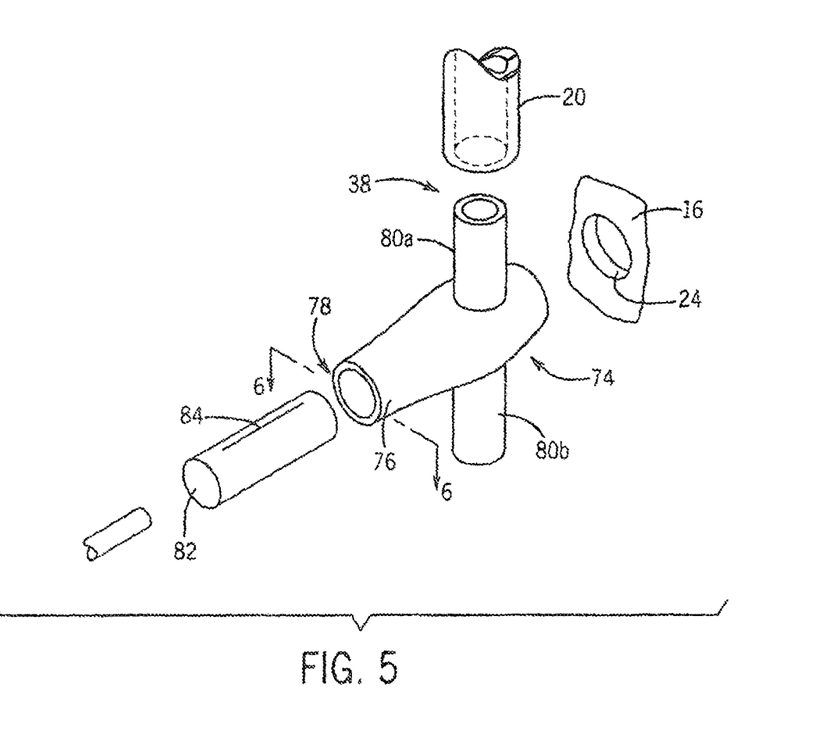
FIG. 5 is a perspective view of a second embodiment of the invention employing a T-tube with a received slotted resilient element.

Referring now to FIG. 5, in an alternative embodiment, the valve 38 may provide for a T-tube 74 including a tubular sleeve 76 defining an internal chamber open at a front end 78 and integrally molded (for example, from thermoplastic) to two intersecting, axially opposed connector tubes 80a and 80b so that the internal chamber of the tubular sleeve 76 communicates with and is positioned along the flow path from tube 80a to tube 80b extending on opposite sides of the tubular sleeve 76. The tube 80a and 80b may receive and retain ends of the fluid line 20 so as to be placed in series with the fluid line 20 by means of barbs, press fit, adhesive, or a welding process.

The opening of the tubular sleeve 76 at the front end 78 is substantially cylindrical to receive and be sealed by a cylindrical elastomeric plug 82 inserted into the tubular sleeve. The elastomeric plug 82 may, for example, be a silicone material. The elastomeric plug 82 has a diametric slot 84 extending along the axis of the elastomeric plug 82. The diametric slot 84 is positioned near the middle of the elastomeric plug 82 to align with the path between the connector tubes 80a and 80b. Elastomeric plug 82 is sized to abut a rear, closed end of the chamber of the tubular sleeve 76 when the diametric slot 84 is aligned with the connector tubes 80.

Figure 6A:
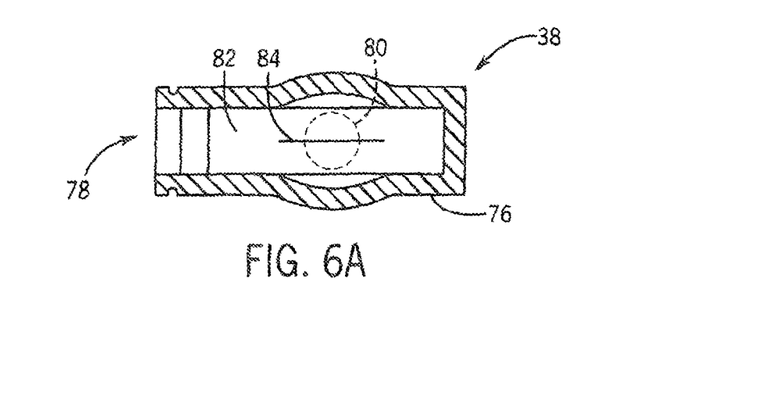
FIGS. 6a and 6b are cross-sectional views along lines 6-6 of FIG. 5 showing respectively the resilient element in a relaxed state blocking flow through the fluid line and in a compressed state allowing flow through the fluid line, the latter figure also showing a cap element holding the resilient element in a compressed state during IV line priming.

Referring now also to FIG. 6a, in a relaxed (relatively uncompressed) state, the diametric slot 84 is held closed by the natural resilience of the elastomeric plug 82 preventing flow through the connector tubes 80a and 80b or into or out of the chamber of the tubular sleeve 76. In some embodiments a flat interface between the elastomeric plug 82 and the openings of the connector tubes 80a and 80b in the tubular sleeve 76 may be provided for improved sealing in this state.

Figure 6B:
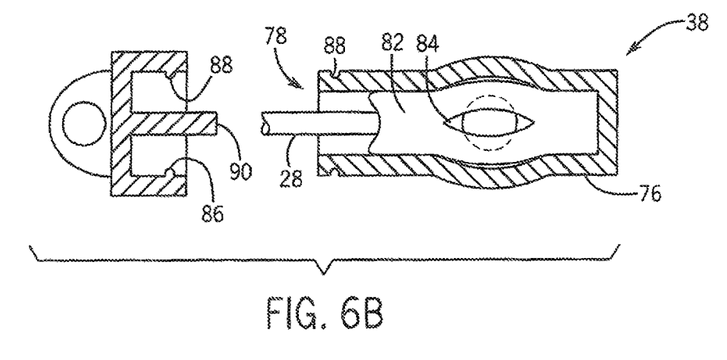

Referring now to FIGS. 1 and 6b, the compressor 29 on the door 26 may be a pin that can be received through the open front end 78 of the tubular sleeve 76 to compress the elastomeric plug 82 along its axis against the closed end of the tubular sleeve 76 causing a deformation of the material of the elastomeric plug 82 such as opens the slot 84 to allow flow between the connector tubes 80a and 80b. The elastomeric plug 82 under such compression tightly seals against the inner surface of the tubular sleeve 76 near the front end 78 to prevent any leakage out of the valve 38 during this time. Removal of the compressor 29 causes the slot 84 to close again as shown in FIG. 6a.

The valve 38 may be shipped with an activation cap 86 attached over the front end 78 and held to the tubular sleeve 76 by snap detent elements 88. This activation cap 86 may include a pin portion 90 extending into the tubular sleeve 76 operating in a manner similar to the compressor 29 shown in FIG. 6b to hold the slot 84 open during initial priming of the fluid line 20. This activation cap 86 is then removed, sealing the fluid line against leakage until it is placed in the pump 12 and the door closed. Although not shown in this figure, the activation cap 86 may be tethered to the tubular sleeve 76, for example, by a molded interconnecting element.

Figure 7:
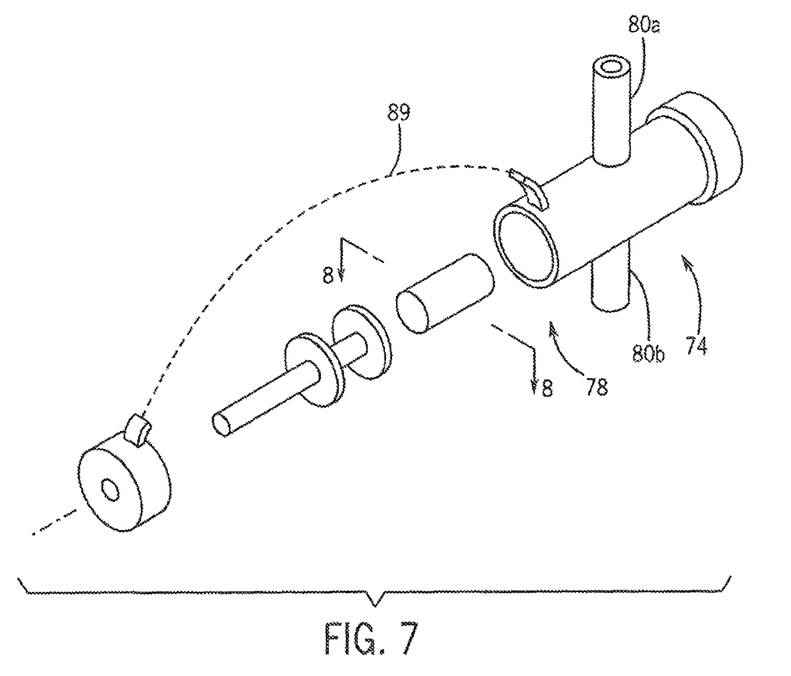
FIG. 7 is a perspective view similar to that of FIG. 5 of a third embodiment having a resilient element and a tandem plunger fitting within a T-tube.
Figure 8A:
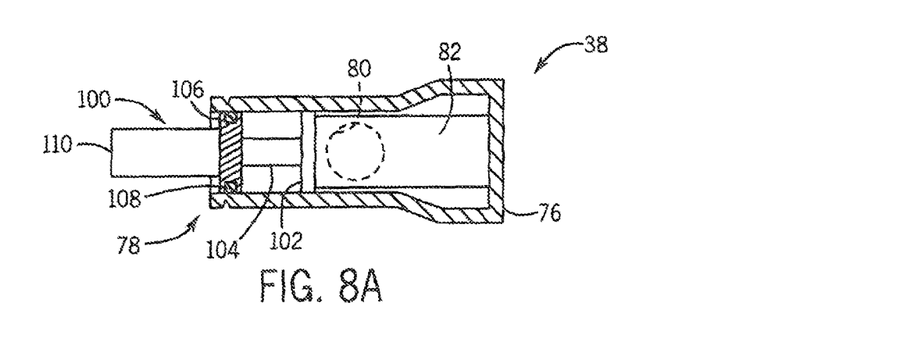
FIGS. 8a and 8b are cross-sectional views along lines 8-8 showing respectively: the resilient element in a relaxed state blocking flow through the fluid line and the resilient element in the compressed state allowing flow through the fluid line, the latter figure also showing a cap element holding the resilient element in a compressed state during IV line priming.
Figure 8B:
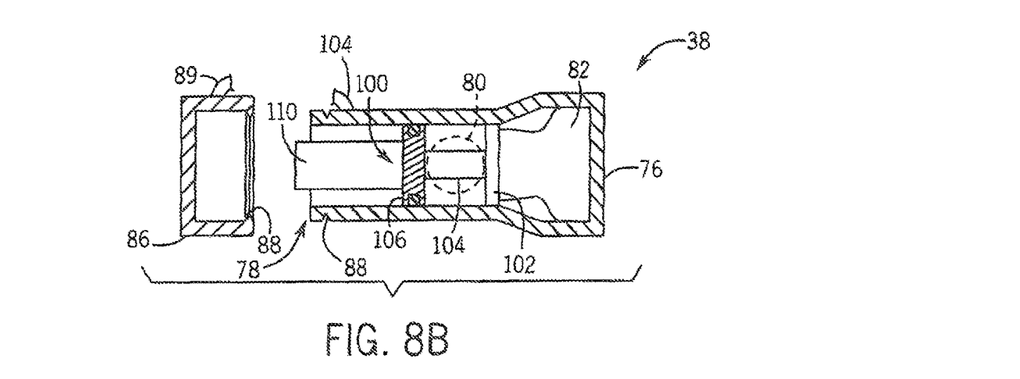

Referring now to FIGS. 7, 8a and 8b, in an alternative embodiment the T-tube 74 may receive a shorter elastomeric plug 82, without a slot, that in a relaxed state blocks the passage of fluid between connector tubes 80a and 80b, as described before, but which may be compressed by a tandem piston assembly 100 to push it away from the connector tubes 80a and 80b to allow flow between the connector tubes 80a and 80b through the fluid line 20.

The tandem piston assembly 100 provides a first plunger element 102 abutting an end of the elastomeric plug 82 nearest to the front end 78 that may perform the compression operation moving the elastomeric plug 82 away from the openings of the connector tubes 80. A short spacer shaft 104 connects the plunger element 102 to a seal disk 106 displaced along the axis of the tubular sleeve 76 toward the front end 78 and having a circumferential seal such as an O-ring 108 fitting tightly against a cylindrical inner surface of the tubular sleeve 76 to prevent fluid flow out of the tubular sleeve 76 past the seal disk 106. When the elastomeric plug 82 is compressed away from the openings of the connector tubes 80, fluid may flow around the spacer shaft 104 but is blocked from exiting the open front end 78 by the seal disk 106.

A short extender shaft 110 may connect to the seal disk 106 and pass out of the open front end 78 of the tubular sleeve 76 when the elastomeric plug 82 is in the relaxed state to engage with a compression compressor 29 on the door as discussed before causing the plunger element 102 to compress the elastomeric plug 82. An activation cap 86 may fit on and be held by means of detent elements 88 over the open front end 78 to press inward on the extender shaft 110 holding the valve 38 in the open state during IV line commission as has been discussed above. After priming, this activation cap 86 may be folded out of the way as attached to the tubular sleeve 76 by a molded tether element 89. Alternatively, the activation cap 86 may be untethered and discarded after use.

Each of the elements of the tubular sleeve 76, the connector tubes 80, and the tandem piston assembly 100 and the tether element 89 may be constructed of injection molded thermoplastic material.

Figure 9:
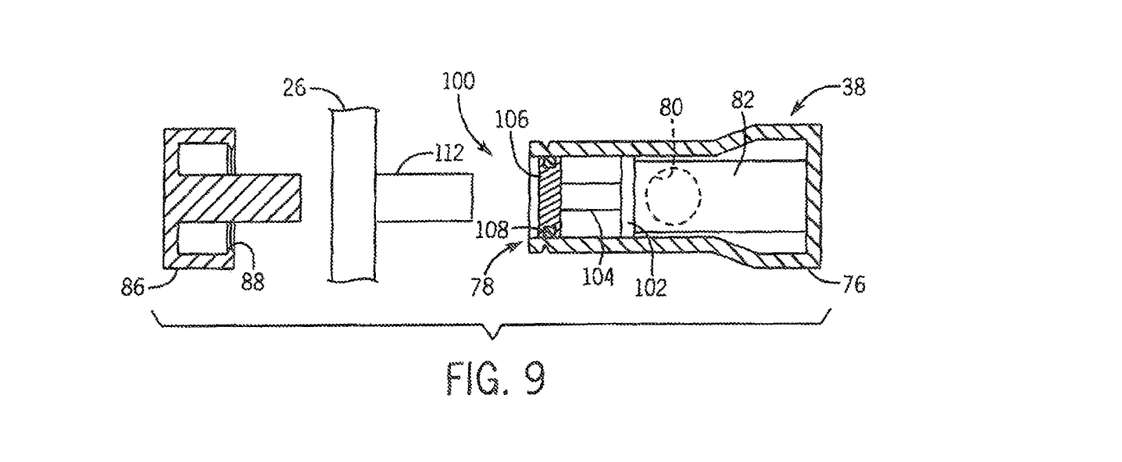
FIG. 9 is a figure similar to that of FIG. 8a showing a modification of the valve using a door affixed activating pin.

Referring now to FIG. 9, in an alternative embodiment, the extender shaft 100 may be removed from the embodiment of FIG. 8 in favor of an activation pin 112 extending inward from the door 26 serving the same purpose as the extender shaft 102 push plunger elements 102 and seal disk 106 inward when the door 26 is closed and flow through the line 20 is desired. In this case, cap 86 may, like cap 86 of FIG. 6, include a pin portion 92 allow priming of the line 20 before the valve 38 is inserted in the pump 12.

Certain terminology is used herein for purposes of reference only, and thus is not intended to be limiting. For example, terms such as "upper", "lower", "above", and "below" refer to directions in the drawings to which reference is made. Terms such as "front", "back", "rear", "bottom" and "side", describe the orientation of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second" and other such numerical terms referring to structures do not imply a sequence or order unless clearly indicated by the context.

When introducing elements or features of the present disclosure and the exemplary embodiments, the articles "a", "an", "the" and "said" are intended to mean that there are one or more of such elements or features. The terms "comprising", "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

It is specifically intended that the present invention not be limited to the embodiments and illustrations contained herein and the claims should be understood to include modified forms of those embodiments including portions of the embodiments and combinations of elements of different embodiments as come within the scope of the following claims. All of the publications described herein, including patents and non-patent publications are hereby incorporated herein by reference in their entireties.

What we claim is:

1. A medical pump comprising:
   a housing providing a door openable to expose a first face for receiving a fluid line therealong, the first face including a valve retention element for receiving a valve of the fluid line;
   a pump providing pump elements exposed at the first face;
   a fluid line kit including a length of a tubing terminating at opposed first and second ends and receivable in the pump elements so that the pump elements may operate to pump liquid through the fluid line; and
   a valve retained on the tubing between the first and second ends and receivable by the valve retention element when the tubing is received in the pump elements, the valve including
   (a) a valve housing positioned between a first portion and a second portion of the tubing to provide a flow path between a first opening into the valve housing communicating with the first portion of the tubing and a second opening in the valve housing communicating with the second portion of the tubing, and
   (b) a fluid blocking element positioned within the valve housing and resiliently biased to block fluid flow along the flow path in a relaxed state and to permit fluid flow along the flow path in a compressed state; and
   (c) a plunger for compressing the fluid blocking element along an axis so that fluid flow may pass the fluid blocking element and the fluid blocking element is displaced away from the fluid flow;
   wherein the valve housing provides an internal chamber fluidly communicating with a lumen of the tubing so that the internal chamber is positioned along the flow path;
   wherein the fluid blocking element is an elastomer element having an elastically deformable volume expanding to block the fluid path by an abutment of the volume against at least one of the first and second openings and prevent flow through the tubing in the relaxed state and compressible to move the volume away from the at least one of the first and second openings to permit flow therethrough in the compressed state;
   wherein the plunger provides a seal to prevent fluid outflow from the internal chamber when the plunger compresses the fluid blocking element and fluid flow passes the fluid blocking element; and
   wherein the door includes an operator element configured to compress the fluid blocking element from the relaxed state to the compressed state when the fluid line kit is installed in the pump and the door is closed.

2. The medical pump of claim 1 wherein the elastomer element, in the relaxed state, fills at least a portion of the internal chamber to block fluid flow between the first and second portions of the tubing and which, in the compressed state, allows fluid flow between the first and second portions of the tubing.

3. The medical pump of claim 1 wherein the tubing includes a bag spike attached to the first end and a luer lock attached to the second end and the valve is retained therebetween.

4. The medical pump of claim 1 wherein the first and second portions of the tubing extend axially from connections on opposite sides of the valve housing.

5. The medical pump of claim 1 wherein the first and second portions of the tubing extend from connections on the valve housing formed by at least one of barbs, press fit, adhesive, and welding.

6. The medical pump of claim 2 wherein the elastomeric element abuts a closed end of the valve housing.

7. The medical pump of claim 1 wherein the operator element and the valve housing provide interengaging lock elements holding the elastomer element in the compressed state when the lock elements are engaged and releasing the elastomeric element in the relaxed state when the interengaging lock elements are disengaged.

8. The medical pump of claim 1 wherein the plunger slides the elastically deformable volume across a surface of at least one of the first and second openings.

9. The medical pump of claim 6 wherein the elastomeric element is compressible from the relaxed state to the compressed state against the closed end of the valve housing.

10. The medical pump of claim 9 wherein the elastomeric element is compressible perpendicular to the flow path between the first and second openings and away from the openings.

11. The medical pump of claim 1 further comprising a cap configured to compress the fluid blocking element from the relaxed state to the compressed state when the cap is received by the valve housing and the valve is removed from the housing.

* * * * *